United States Patent [19]

Kaulen

[11] Patent Number: 4,988,823
[45] Date of Patent: Jan. 29, 1991

[54] OPTICALLY ACTIVE OXIRANES

[75] Inventor: Johannes Kaulen, Bergisch Gladbach, Fed. Rep. of Germany

[73] Assignee: Bayer Aktiengesellschaft, Leverkusen, Fed. Rep. of Germany

[21] Appl. No.: 372,062

[22] Filed: Jun. 27, 1989

[30] Foreign Application Priority Data

Jul. 8, 1988 [DE] Fed. Rep. of Germany ....... 3823174

[51] Int. Cl.$^5$ .................. C07D 327/06; C07D 411/04; C07D 497/04
[52] U.S. Cl. ...................................... 549/14; 549/15; 549/16
[58] Field of Search ............................. 549/14, 15, 16

[56] References Cited

U.S. PATENT DOCUMENTS

| | | | |
|---|---|---|---|
| 3,641,054 | 2/1972 | Martin | 549/14 |
| 4,220,561 | 9/1980 | Winter et al. | 549/14 |
| 4,855,438 | 8/1989 | Kaulen et al. | 548/267.8 |

FOREIGN PATENT DOCUMENTS

| | | |
|---|---|---|
| 0040345 | 5/1981 | European Pat. Off. |
| 0052424 | 10/1981 | European Pat. Off. |
| 0061835 | 10/1982 | European Pat. Off. |
| 0084834 | 1/1983 | European Pat. Off. |
| 0124009 | 4/1984 | European Pat. Off. |
| 0124011 | 4/1984 | European Pat. Off. |
| 0124013 | 4/1984 | European Pat. Off. |
| 0124014 | 4/1984 | European Pat. Off. |

*Primary Examiner*—Frederick E. Waddell
*Assistant Examiner*—Catherine S. Kilby Scalzo
*Attorney, Agent, or Firm*—Sprung Horn Kramer & Woods

[57] ABSTRACT

Optically active oxiranes of the formula

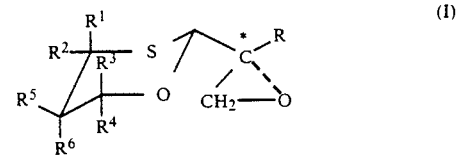

in which

R represents substituted or unsubstituted alkyl, substituted or unsubstituted cycloalkyl or represents substituted or unsubstituted phenyl, and $R^1$, $R^2$, $R^3$, $R^4$, $R^5$ and $R^6$ represent hydrogen or alkyl, at least one of the radicals representing alkyl, or $R^4$ and $R^5$ together represent alkanediyl, which is unsubstituted or substituted by alkyl, or $R^4$ and $R^5$ together with the adjacent carbon atoms represent a fused bicyclic hydrocarbon radical, which is unsubstituted or substituted by alkyl are produced by reacting an enantiomerically pure oxathiane ketone of the formula

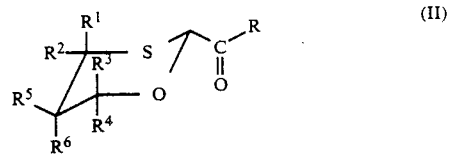

with a sulphonium or sulphoxonium salt. The product can be converted to optically active 2-hydroxyethylazole derivatives of the formula

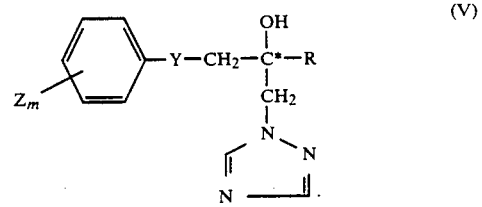

4 Claims, No Drawings

OPTICALLY ACTIVE OXIRANES

The present invention relates to novel optically active oxiranes, a new process for their preparation and their use as intermediates for the synthesis of active substances having optical activity and fungicidal and plant growth regulating properties.

Racemates of a large number of oxiranes have already been disclosed (cf. EP-OS (European Published Specification) No. 0,040,345, EP-OS (European Published Specification) No. 0,052,424, EP-OS (European Published Specification) No. 0,061,835 and EP-OS (European Published Specification) No. 0,084,834). However, the corresponding oxiranes are not available without difficulties due to the reactivity of the oxirane ring.

Furthermore it is known that oxiranes can be prepared by reaction of the underlying ketones with sulphonium or sulphoxonium ylides (EP-OS (European Published Specification) No. 0,040,345, EP-OS (European Published Specification) No. 0,124,009, EP-OS (European Published Specification) No. 0,124,011, EP-OS (European Published Specification) No. 0,124,013 and EP-OS (European Published Specification) No. 0,124,014). However, the disadvantage of the known processes is that no optically active oxiranes are thereby available in a stereospecific manner.

Novel optically active oxiranes of the formula

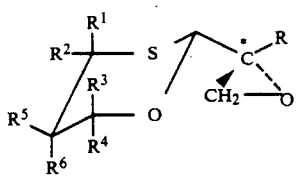

(I)

in which
R represents substituted or unsubstituted alkyl, substituted or unsubstituted cycloalkyl or substituted or unsubstituted phenyl and $R^1$, $R^2$, $R^3$, $R^4$, $R^5$ and $R^6$ represent hydrogen or alkyl, where, however, at least one of the radicals represents alkyl, or
$R^4$ and $R^5$ together represent alkanediyl which is unsubstituted or substituted by alkyl, or
$R^4$ and $R^5$ together with the adjacent carbon atoms represent a fused bicyclic hydrocarbon radical, which is unsubstituted or substituted by alkyl,
have now been found.

Furthermore it has been found that optically active oxiranes of the formula (I) can be prepared by reacting enantiomerically pure oxathiane ketones of the formula

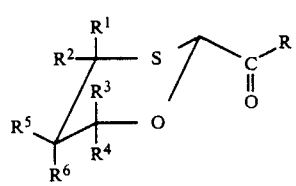

(II)

in which
R, $R^1$, $R^2$, $R^3$, $R^4$, $R^5$ and $R^6$ have the abovementioned meanings,
either (α) with sulphonium salts of the formula

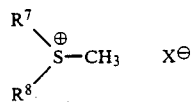

(III)

in which
$R^7$ represents methyl or phenyl,
$R^8$ represents methyl or phenyl and
$X^\ominus$ represents halide or methosulphate,
or
(β) with sulphoxonium salts of the formula

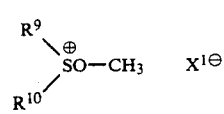

(IV)

in which
$R^9$ represents methyl or phenyl,
$R^{10}$ represents methyl or phenyl and
$X^{1\ominus}$ represents halide or methosulphate,
in the presence of a strong base and in the presence of a diluent at temperatures between −78° C. and +100° C.

Finally it has been found that optically active oxiranes of the formula (I) can be used as intermediates for the preparation of active substances having optical activity and fungicidal and plant-growth regulating properties. Thus optically active 2-hydroxyethylazole derivatives of the formula

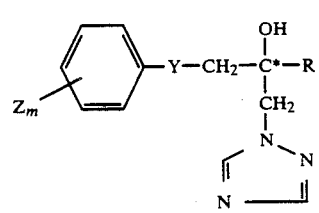

(V)

in which
R has the abovementioned meaning,
Y represents oxygen, a direct bond or a CH₂ group,
represents halogen, alkyl, cycloalkyl, alkoxy, alkylthio, halogenoalkyl, halogenoalkoxy, halogenoalkylthio, substituted or unsubstituted phenoxy, substituted or unsubstituted phenylalkyl or substituted or unsubstituted phenoxyalkyl and
m represents the numbers 0, 1, 2 or 3,
are obtained by reacting optically active oxiranes of the formula

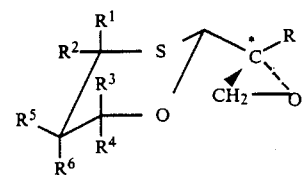

(I)

in which
R, $R^1$, $R^2$, $R^3$, $R^4$, $R^5$ and $R^6$ have the abovementioned meanings,
in a first step either
(γ) with phenol derivatives of the formula

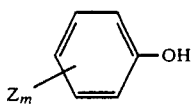

in which
Z and m have the abovementioned meanings, in the presence of a base and in the presence of a diluent at temperatures between 0° C. and 150° C., or (δ) with Grignard compounds of the formula

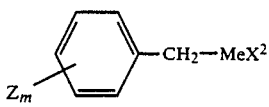

in which
Z and m have the abovementioned meanings,
Me represents an alkaline earth metal or zinc and
$X^2$ represents chlorine, bromine or iodine,
in the presence of a diluent at temperatures between $-78°$ C. and $+100°$ C., subsequently reacting the optically active compounds of the formula

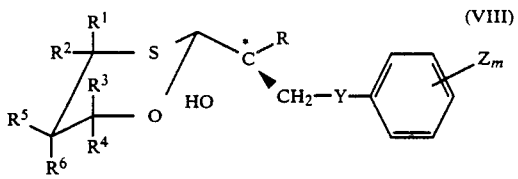

in which R, $R^1$, $R^2$, $R^3$, $R^4$, $R^5$, $R^6$, Y, Z and m have the above-mentioned meanings thus obtained in a second step with a reagent suitable for the cleavage of oxathiane compounds in the presence of a diluent and, if required, in the presence of an acid-binding agent at temperatures between 0° C. and 100° C. and reacting the optically active α-hydroxyaldehydes thereby formed of the formula

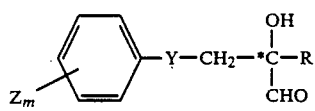

in which R, Y, Z and m have the abovementioned meanings, with a reagent suitable for the reduction of aldehydes in the presence of a diluent at temperatures between $-20°$ C. and $+100°$ C., furthermore in a third step reacting the optically active diols thus obtained of the formula

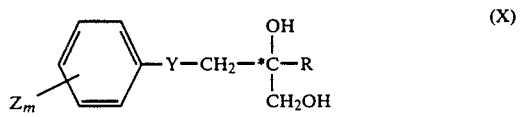

in which R, Y, Z and m have the abovementioned meanings, with sulphonic acid derivatives of the formula:

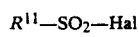

in which
$R^{11}$ represents alkyl, halogenoalkyl or substituted or unsubstituted phenyl and
Hal represents for halogen,
in the presence of a diluent and in the presence of an acid-binding agent at temperatures between 0° C. and 100° C. and finally in a fourth step reacting the resulting optically active compounds of the formula

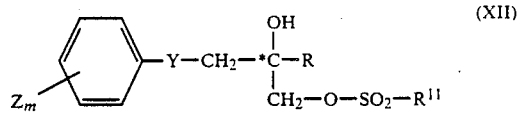

in which R, $R^{11}$, Y, Z and m have the abovementioned meanings, with triazole salts of the formula

in which
$Me^1$ represents an alkali metal,
in the presence of a diluent and, if required, in the presence of an acid-binding agent at temperatures between 20° C. and 150° C.

In the present case, the steric constitution of the individual groups has been indicated in the drawings of the formulae only in some cases. Furthermore asymmetrically substituted carbon atoms have been marked by a (*) if they are optically active compounds. In addition to the marked carbon atoms, further asymmetrically substituted carbon atoms can additionally be present.

The course of the process according to the invention for the preparation of optically active oxiranes of the formula (I) must be considered as extremely surprising. Thus it could not have been expected that the very reactive ylides which are formed as intermediates upon treatment of the sulphonium salts of the formula (III) or sulphoxonium salts of the formula (IV) with strong bases would react stereoselectively with oxathiane ketones of the formula (II). Rather it had to be assumed that the sulphur ylides, owing to their high reactivity, would attack the carbonyl group in such a manner that mixtures are formed in which the two forms of the optically active oxiranes of the formula (I) are present in almost equal parts.

It is also surprising that the optically active oxiranes of the formula (I) can be converted to optically active 2-hydroxyethylazole derivatives of the formula (V) with a high selectivity and in a very good yield. This is because due to the multi-step character of the synthesis it had to be expected that side reactions would occur and the respective undesired enantiomer would in each case also be present in a relatively large amount in the final product in addition to the desired enantiomer.

The process according to the invention for the preparation of the optically active oxiranes of the formula (I) is distinguished by a series of advantages. Thus the oxathiane ketones required as starting materials are available in their enantiomerically pure form and are, like the required reaction components, also available in fairly large amounts. Furthermore the reaction and the workup do not present any difficulties. However, the most decisive advantage is that the optically active oxiranes can be prepared stereospecifically by a direct synthesis and no resolutions of racemates have to be carried out.

The process for the preparation of optically active 2-hydroxyethylazole derivatives of the formula (V) likewise has significant advantages. In their case, too, the reaction components used are only conventional chemicals which are available even in large amounts and are easy to handle. Furthermore in their case, too, the individual reactions and the workup of the reaction products which are formed in each case do not present any difficulties. Finally it is particularly favorable that in the asymmetrical total synthesis of the optically active 2-hydroxyethylazole derivatives of the formula (V), all of the starting material is converted to the respective enantiomer desired.

Formula (I) provides a general definition of the optically active oxiranes according to the invention. Those compounds of the formula (I) are preferred in which R represents a straight-chain or branched alkyl having 1 to 6 carbon atoms, which is unsubstituted or substituted by halogen, alkoxy having 1 to 4 carbon atoms, alkylthio having 1 to 4 carbon atoms, the CHO group and derivatives thereof, phenoxy and/or phenyl, represents cycloalkyl having 3 to 8 carbon atoms, which is unsubstituted or substituted by alkyl having 1 to 4 carbon atoms, alkoxy having 1 to 4 carbon atoms, alkylthio having 1 to 4 carbon atoms and/or halogen or represents phenyl, which is unsubstituted or substituted by alkyl having 1 to 4 carbon atoms, alkoxy having 1 to 4 carbon atoms, alkylthio having 1 to 4 carbon atoms and/or halogen and $R^1$, $R^2$, $R^3$, $R^4$, $R^5$ and $R^6$ represent hydrogen or alkyl having 1 to 4 carbon atoms, where, however, at least one of these radicals represents alkyl having 1 to 4 carbon atoms, or furthermore $R^4$ and $R^5$ together may represent alkanediyl having 3 to 6 carbon atoms, which is unsubstituted or monosubstituted to trisubstituted by identical or different substituents from the series comprising alkyl having 1 to 4 carbon atoms or furthermore $R^4$ and $R^5$ together with the adjacent carbon atoms may represent a fused bicyclic hydrocarbon having 7 or 8 carbon atoms, which is unsubstituted or monosubstituted to trisubstituted by identical or different substituents from the series comprising alkyl having 1 to 4 carbon atoms.

Particular preference is given to those optically active compounds of the formula (I) in which R represents alkyl having 1 to 4 carbon atoms, which is unsubstituted or substituted by fluorine, chlorine, bromine, alkoxy having 1 or 2 carbon atoms, dioxolanyl, formyl, methoximinomethyl, alkylthio having 1 or 2 carbon atoms, phenoxy and/or phenyl, represents cycloalkyl having 3 to 7 carbon atoms, which is unsubstituted or substituted by alkyl having 1 or 2 carbon atoms, alkoxy having 1 or 2 carbon atoms, alkylthio having 1 or 2 carbon atoms, fluorine, chlorine and/or bromine or represents phenyl, which is unsubstituted or substituted by alkyl having 1 or 2 carbon atoms alkoxy having 1 or 2 carbon atoms, alkylthio having 1 or 2 carbon atoms, fluorine, chlorine and/or bromine and $R^1$, $R^2$, $R^3$, $R^4$, $R^5$ and $R^6$ represent hydrogen, methyl or ethyl, where, however, at least one of these radicals represents methyl or ethyl, or furthermore $R^4$ and $R^5$ together may represent alkanediyl having 3 to 5 carbon atoms, which is unsubstituted or monsubstituted to trisubstituted by identical or different substituents from the series comprising methyl and/or ethyl, or furthermore $R^4$ and $R^5$ together with the adjacent carbon atoms may represent a fused bicyclic hydrocarbon having 7 or 8 carbon atoms, which is unsubstituted or monosubstituted to trisubstituted by identical or different substituents from the series comprising methyl and/or ethyl.

Very particular preference is given to those optically active oxiranes of the formula (I) in which R represents methyl, ethyl, isopropyl or tert.-butyl, which is unsubstituted or monosubstituted or disubstituted by identical or different substituents from the series comprising fluorine, chlorine, bromine, methoxy, methylthio, methoximinomethyl, phenoxy and/or phenyl, furthermore represents the grouping

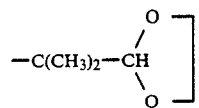

furthermore represents cyclopropyl, cyclopentyl or cyclohexyl, each of which is unsubstituted or monosubstituted or disubstituted by identical or different substituents from the series comprising methyl, methylthio, fluorine and/or chlorine, or represents phenyl which is unsubstituted or monosubstituted or disubstituted by identical or different substituents from the series comprising methyl, methoxy, methylthio, fluorine and/or chlorine, and the oxathiane moiety represents groupings of the formulae

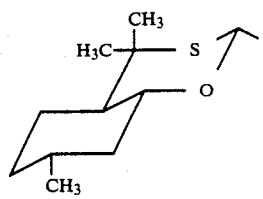

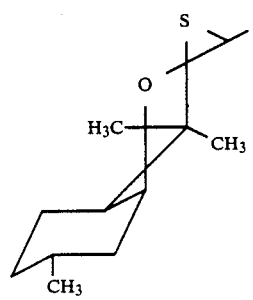

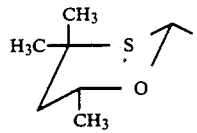

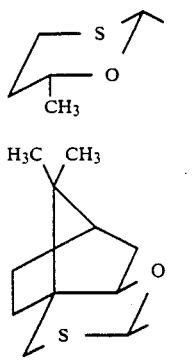

or

If enantiomerically pure oxathiane ketone of the formula (II-1) is used as the starting material, trimethylsulphoxonium iodide as the reaction component and potassium tert.-butylate as the base, when the process according to the invention is carried out, the course of the reaction can be illustrated by the following formula scheme:

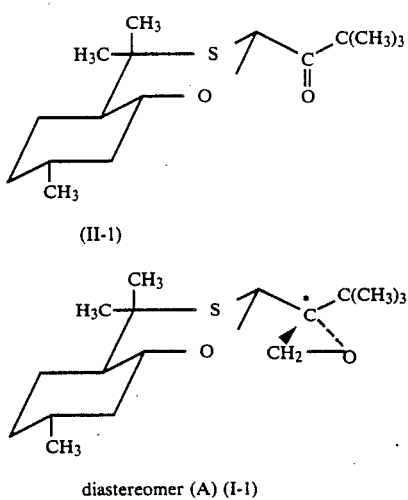

diastereomer (A) (I-1)

Which of the two diastereomers possible (A) and (B) is formed in the reaction according to the invention, depends on the steric structure of the oxathiane ketone used.

Formula (II) provides a general definition of the enantiomerically pure oxathiane ketones which are required as starting materials, when the process according to the invention is carried out. In this formula, R, $R^1$, $R^2$, $R^3$, $R^4$, $R^5$ and $R^6$ preferably have those meanings which have already been mentioned as preferred for these radicals in connection with the description of the substances according to the invention of the formula (I). The enantiomerically pure oxathiane ketones of the formula (II) are known or can be prepared by methods which are known in principle (cf. DE-OS (German Published Specification) No. 3,627,673).

Formula (III) provides a general definition of the sulphonium salts required as reaction components, when the process according to the invention (variant α) is carried out. Preference is given to those compounds of the formula (III) in which $R^7$ represents methyl or phenyl, $R^8$ represents methyl or phenyl and $X^\ominus$ represents chloride, bromide, iodide or methosulphate.

Formula (IV) provides a general definition of the sulphoxonium salts required as reaction components, when the process according to the invention (variant β) is carried out. Preference is given to those compounds of the formula (IV) in which $R^9$ represents methyl or phenyl, $R^{10}$ represents methyl or phenyl and $X^\ominus$ represents chloride, bromide, iodide or methosulphate.

Both the sulphonium salts of the formula (III) and the sulphoxonium salts of the formula (IV) are known or can be prepared by known methods (cf. J. Amer. Chem. Soc. 87, 1353-1364 (1965) and EP-OS (European Published Specification) 0,040,345).

When the process according to the invention is carried out, in both variant α and variant β, all customary strong inorganic and organic bases can be used as bases. Preferably, sodium hydride, sodium amide and alkali metal hydroxides, such as, for example, sodium hydroxide or potassium hydroxide, and also alkali metal alcoholates, such as sodium methylate, sodium ethylate and potassium tert.-butylate, can be used.

When the process according to the invention is carried out, in the procedure according to both variant α and variant β, any inert organic solvent customary for this type of reaction can be used as diluent. Preferably, nitriles, such as acetonitrile, furthermore alcohols, such as methanol, ethanol, propanol, n-butanol and tert.-butanol, and also polar solvents, such as dimethyl sulphoxide, furthermore aromatic or aliphatic hydrocarbons, such as hexane, benzene, toluene and xylene, and finally also dimethyl sulphide or dimethyl sulphate can be used.

When the process according to the invention is carried out, in the procedure according to both variant α and variant β, the reaction temperatures can be varied within a certain range. In general, the reaction is carried out at temperatures between −78° C. and +100° C., preferably between 0° C. and 60° C.

The process according to the invention is in general carried out under atmospheric pressure. However, it is also possible to employ superatmospheric or reduced pressure.

When the process according to the invention is carried out, the amounts of reaction components are chosen such that in general 1.0 to 2.0 moles, preferably 1.1 to 1.8 moles, of sulphonium salt of the formula (III) or of sulphoxonium salt of the formula (IV) and 1.0 to 2.5 moles, preferably 1.3 to 2.0 moles, of base are present per mole of enantiomerically pure oxathiane ketone of the formula (II).

In detail, the process according to the invention is carried out such that a mixture of enantiomerically pure oxathiane ketone of the formula (II) and freshly prepared sulphonium salt of the formula (III) or sulphoxonium salt of the formula (IV) in a diluent is treated with the strong base in the absence or presence of an inert gas atmosphere, and the mixture is stirred. The subsequent workup is carried out by conventional methods. In general, the procedure is such that the reaction mixture is first concentrated by evaporating the diluent, the residue is treated with water, the resulting mixture is extracted with an organic solvent which has low miscibility with water, and the combined organic phases are dried and concentrated. The resulting product can, if necessary, be freed from any undesired substances which may still be present by conventional methods, for example by purification using column chromatography.

The optically active oxiranes according to the invention of the formula (I) are, as already mentioned, valuable intermediates for the synthesis of optically active 2-hydroxyethylazole derivatives having fungicidal and plant-growth regulating properties.

If, when carrying out variant γ of the process for the preparation of compounds of the formula (V), optically active oxirane of the formula (I-1) and 4-chlorophenol are used as starting materials, N-chlorosuccinimide and silver nitrate as the reagent for cleaving the oxathiane compound in the second step and lithium alumin hydride for the reduction of the aldehyde in the second step, chloromethanesulphonic acid as reaction component in the third step and the sodium salt of 1,2,4-triazole as reactant in the fourth step, the course of the reaction can be illustrated by the following formula scheme:

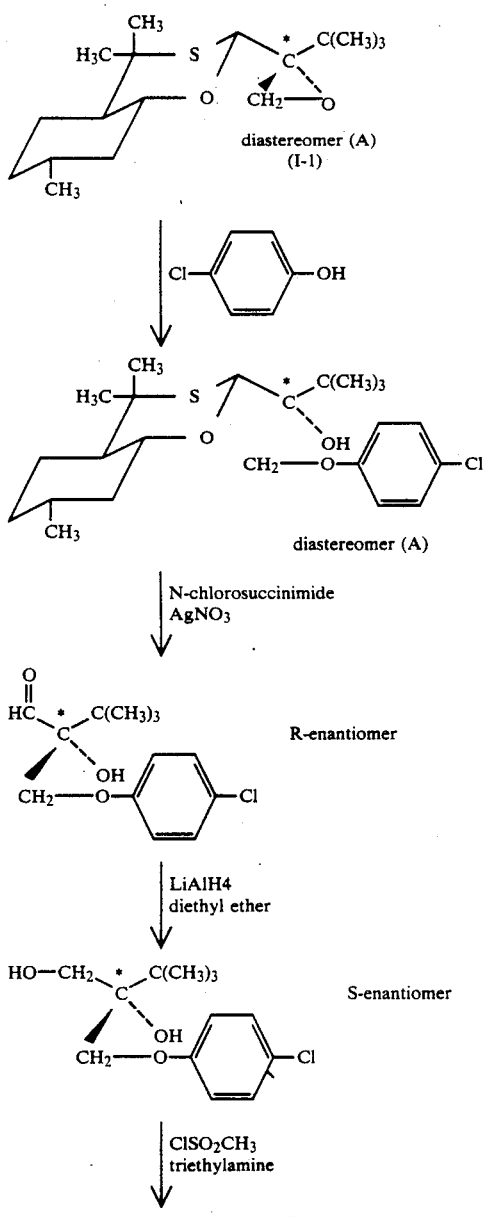

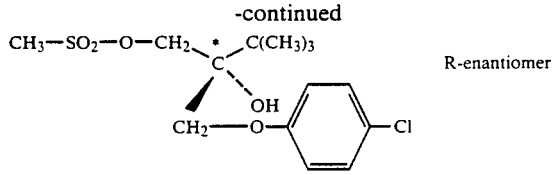

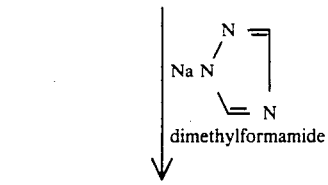

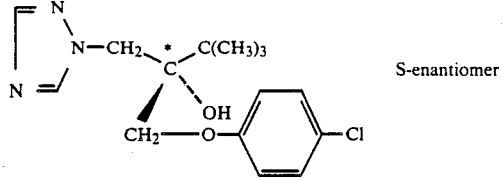

If, when carrying out variant δ of the process for the preparation of compounds of the formula (V), optically active oxirane of the formula (I-1) and 4-chlorobenzylmagnesium bromide are used as starting materials, N-chlorosuccinimide and silver nitrate as the reagents for cleaving the oxathiane compound in the second step and lithium aluminum hydride for the reduction of the aldehyde in the second step, chloromethanesulphonic acid as reaction component in the third step and the sodium salt of 1,2,4-triazole as reactant in the fourth step, the course of the reaction can be illustrated by the following formula scheme:

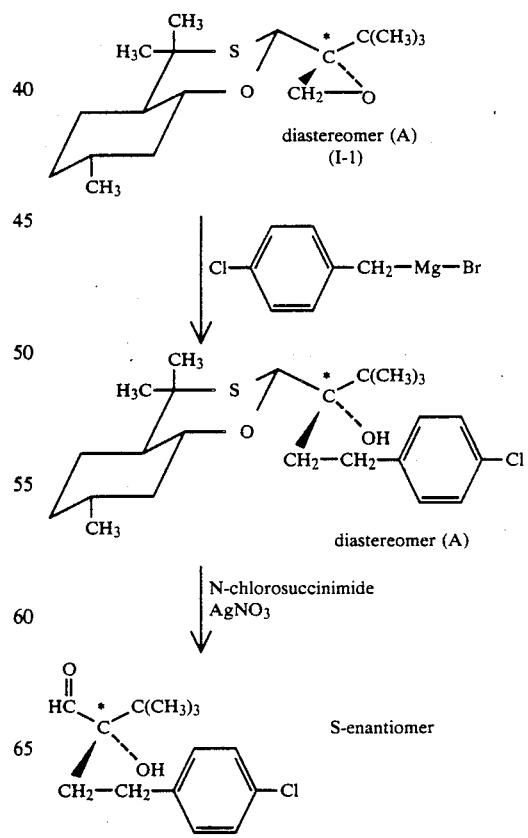

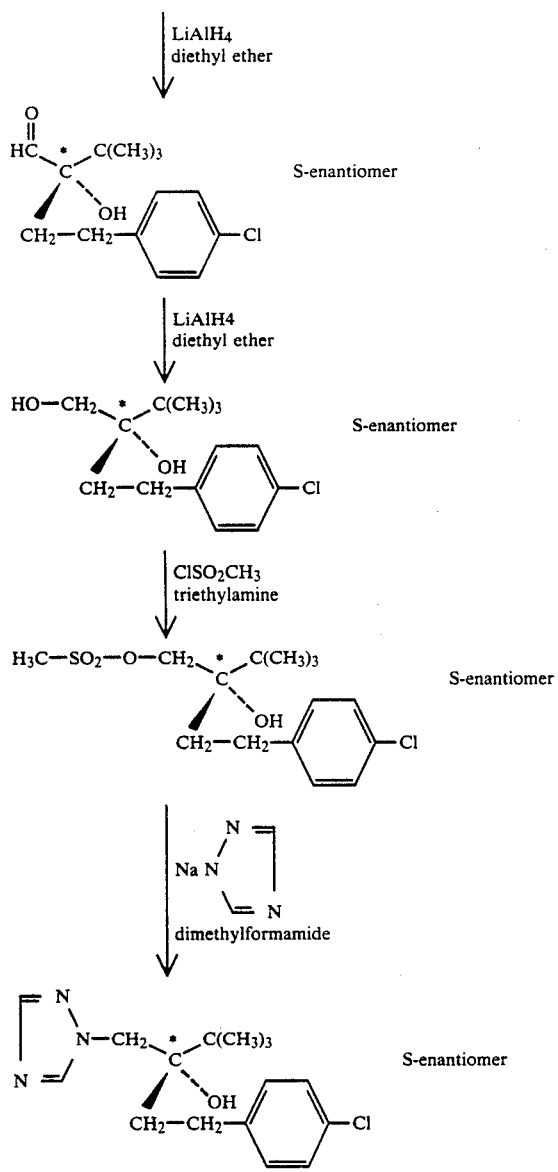

In the above formula drawings and also in the subsequent part of the description, the assignment of the configuration "R" or "S" in each case refers to the carbinol carbon atom.

Formula (VI) provides a general definition of the phenol derivatives required as reaction components, when the variant γ of the process for the preparation of optically active 2-hydroxyethylazole derivatives of the formula (V) is carried out. Preference is given to compounds of the formula (VI) in which Z represents fluorine, chlorine, bromine, alkyl having 1 to 4 carbon atoms, cycloalkyl having 3 to 8 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, phenyl which is unsubstituted or substituted by halogen and/or alkyl having 1 to 4 carbon atoms, phenoxy which is unsubstituted or substituted by halogen and/or alkyl having 1 to 4 carbon atoms, phenylalkyl which has 1 or 2 carbon atoms in the alkyl moiety and which is unsubstituted or substituted by halogen and/or alkyl having 1 to 4 carbon atoms or represents phenylalkoxy which has 1 or 2 carbon atoms in the alkoxy moiety and which is unsubstituted or substituted by halogen and/or alkyl having 1 to 4 carbon atoms, and m represents the number 0, 1, 2 or 3.

Particular preference is given to those phenol derivatives of the formula (VI) in which Z represents fluorine, chlorine, bromine, alkyl having 1 to 4 carbon atoms, cycloalkyl having 3 to 7 carbon atoms, alkoxy having 1 or 2 carbon atoms, alkylthio having 1 or 2 carbon atoms, halogenomethyl having 1 to 3 identical or different halogen atoms, halogenomethoxy having 1 to 3 identical or different halogen atoms, halogenomethylthio having 1 to 3 identical or different halogen atoms, phenyl which is unsubstituted or substituted by fluorine, chlorine and/or methyl, phenoxy which is unsubstituted or substituted by fluorine, chlorine and/or methyl, benzyl which is unsubstituted or substituted by fluorine, chlorine and/or methyl, or represents benzyloxy which is unsubstituted or substituted by fluorine, chlorine and/or methyl, and m represents the numbers 0, 1, 2 or 3.

Very particular preference is given to those substances of the formula (VI) in which Z represents fluorine, chlorine, bromine, methyl, ethyl, isopropyl, tert.-butyl, cyclopropyl, cyclopentyl, cyclohexyl, methoxy, methylthio, trifluoromethyl, trifluoromethoxy, trifluoromethylthio, phenyl which is unsubstituted or monosubstituted or disubstituted by identical or different constituents from the series comprising fluorine, chlorine and/or methyl, phenoxy which is unsubstituted or monosubstituted or disubstituted by identical or different substituents from the series comprising fluorine, chlorine and/or methyl, benzyl which is unsubstituted or monosubstituted or disubstituted by identical or different substituents from the series comprising fluorine, chlorine and/or methyl, or represents benzyloxy which is unsubstituted or monosubstituted or disubstituted by identical or different substituents from the series comprising fluorine, chlorine and/or methyl, and m represents the numbers 0, 1, 2 or 3.

The phenol derivatives of the formula (VI) are generally known compounds of organic chemistry.

The bases which can be used, when the variant γ of the process for the preparation of the optically active compounds of the formula (V) is carried out, are any acid-binding agents which are customary for this type of reaction. Preferably, hydrides, such as sodium hydride, furthermore alkali metal hydroxides and alkali metal carbonates, such as sodium hydroxide, potassium hydroxide, sodium carbonate and potassium carbonate, and in addition also alkali metal alcoholates, such as sodium methylate, sodium ethylate and potassium tert.-butylate, can be used.

The diluents which can be used, when the variant γ of the process for the preparation of the optically active compounds of the formula (V) is carried out, are all inert organic solvents customary for this type of reaction. Preferably, alcohols, such as methanol, ethanol, n-propanol, isopropanol, n-butanol and tert.-butanol, and also strongly polar solvents, such as dimethylformamide, dimethyl sulphoxide and acetonitrile, are used.

When the variant γ of the process for the preparation of the optically active compounds of the formula (V) is carried out, the reaction temperatures can be varied within a fairly large range. In general, the reaction is carried out at temperatures between 0° C. and 150° C., preferably between 10° C. and 130° C.

The reaction according to the variant γ of the process for the preparation of the optically active compounds of the formula (V) is in general carried out under atmospheric pressure. However, it is also possible to employ superatmospheric or reduced pressure.

When the variant γ of the process for the preparation of the optically active compounds of the formula (V) is carried out, in general 1 to 5 moles, preferably 2 to 4 moles of phenol derivative of the formula (VI) and also 1 to 5 moles, preferably 2.5 to 4 moles, of base are used per mole of optically active oxirane of the formula (I). The workup is carried out by conventional methods. In general, the procedure is such that the reaction mixture is first concentrated, then treated with water, then extracted with an organic solvent which has low miscibility with water, the combined organic phases are washed, then dried and concentrated by evaporation of the diluent under reduced pressure and, if necessary, the remaining residue is purified by conventional methods.

Formula (VII) provides a general definition of the Grignard compounds required as reaction components, when the variant δ of the process for the preparation of the optically active compounds of the formula (V) is carried out. In this formula, Z and m preferably have those meanings which have already been mentioned as preferred for this radical and this index in connection with the description of the phenol derivatives of the formula (VI). Me preferably represents magnesium or zinc, and $X^2$ represents chlorine, bromine or iodine.

The Grignard compounds of the formula (VII) are known or can be prepared by processes which are known in principle.

The diluents used, when the variant δ for the preparation of the optically active compounds of the formula (V) is carried out, can be all organic solvents customary for this type of reaction. Preferably, ethers, such as diethyl ether, tetrahydrofuran and dioxane, can be used.

When the variant δ of the process for the preparation of the optically active compounds of the formula (V) is carried out, the reaction temperature can be varied within a certain range. In general, the reaction is carried out at temperatures between −78° C. and +100° C., preferably between −78° C. and +90° C.

The reaction according to the variant δ of the process for the preparation of the optically active compounds of the formula (V) is in general carried out under atmospheric pressure.

When the variant δ of the process for the preparation of the optically active compounds of the formula (V) is carried out, in general 1 to 3 moles, preferably 1 to 1.5 moles, of a Grignard compound of the formula (VII) are used per mole of optically active oxirane of the formula (I). The workup is carried out by conventional methods. In general, the procedure is such that aqueous ammonium chloride solution is added to the reaction mixture, the organic phase is separated off, the aqueous phase is extracted several times with an organic solvent which has a low miscibility with water, the combined organic phases are dried, concentrated and subjected to incipient distillation under reduced pressure. Further purification, which may be necessary, can be carried out by conventional methods.

When the second step of the process for the preparation of the optically active compounds of the formula (V) is carried out, the reagents used for the cleavage of the compounds of the formula (VIII) can be all substances customary for such purposes. Preferably, mixtures of N-chlorosuccinimide and silver nitrate can be used.

When the cleavage of the oxathiane compounds of the formula (VIII) is carried out, the diluents used can be all solvents customary for this type of reaction. Preferably, mixtures of water and polar organic diluents which are miscible with water can be used. Suitable examples are mixtures of acetonitrile and water.

When the cleavage of the oxathiane compounds of the formula (VIII) is carried out, the acid-binding agents used can be all acid acceptors customary for this type reaction. Preferably, alkali metal carbonates and alkali metal bicarbonates, such as, for example, sodium bicarbonate, can be used.

When the cleavage of the oxathiane compounds of the formula (VIII) in the second step of the process for the preparation of the optically active compounds of the formula (V) is carried out, the reaction temperatures can be varied in a fairly large range. In general, the reaction is carried out at temperatures between 0° C. and 100° C., preferably between 20° C. and 60° C.

When cleavage of the oxathiane compounds of the formula (VIII) is carried out, in general 1 to 3 moles of cleavage reagent and also an excess of acid-binding agent are used per mole of the compound of the formula (VIII). The workup is carried out by conventional methods. In general, the procedure is such that aqueous salt solutions are added to the reaction mixture, the solid components are filtered off, the filtrate is extracted several times with organic solvents which have low solubility in water, the combined organic phases are washed, dried and concentrated. The resulting product can be used without any further purification for the subsequent reactions.

When the second step of the process for the preparation of the optically active compounds of the formula (V) is carried out, the reagents used for the reduction of the optically active α-hydroxyaldehydes of the formula (IX) are preferably complex hydrides, such as lithium aluminum hydride and sodium borohydride.

Suitable diluents for the reduction of the optically active α-hydroxyaldehydes of the formula (IX) are all inert organic solvents. Preferably, ethers, such as diethyl ether or tetrahydrofuran, can be used. If sodium borohydride is used as the reducing agent, it is also possible to use alcohols, such as methanol or ethanol, or nitriles, such as acetonitrile, undiluted or in a mixture with water, as the diluent.

When the reduction in the second step of the process for the preparation of the optically active compounds of the formula (V) is carried out, the reaction temperatures can be varied within a certain range. In general, the reaction is carried out at temperatures between −20° C. and +100° C., preferably between 20° C. and 60° C.

When the reduction in the second step of the process for the preparation of the optically active compounds of the formula (V) is carried out, in general 1 to 5 moles of reducing agent are used per mole of optically active α-hydroxyaldehyde of the formula (IX). The workup is carried out by conventional methods. In general, the procedure is such that an organic solvent which has a low solubility in water and also aqueous alkali metal hydroxide solution is added to the reaction mixture, the solid components present are filtered off with suction, and the organic phase, after drying, is concentrated. However, it is also possible first to concentrate the reaction mixture after the reaction is complete, to extract the remaining product with an organic solvent which has a low solubility in water, to dry the combined organic phases and subsequently to concentrate them. The resulting product can be used, with or without previous purification, for the subsequent reactions.

Formula (XI) provides a general definition of the sulphonic acid derivatives required as reaction components, when the third step of the process for the preparation of the optically active compounds of the formula (V) is carried out. Preferably, sulphonic acid derivatives of the formula (XI) are used in which $R^{11}$ represents alkyl having 1 to 4 carbon atoms, halogenoalkyl having 1 or 2 carbon atoms and 1 to 5 halogen atoms or represents phenyl which is unsubstituted or substituted by methyl and Hal represents chlorine or bromine.

Suitable examples of sulphonic acid derivatives of the formula (XI) are: methanesulphonyl chloride, ethanesulphonyl chloride, trifluoromethanesulphonyl chloride and p-tolylsulphonyl chloride.

The sulphonic acid derivatives of the formula (XI) are generally known compounds of organic chemistry.

When the third step of the process for the preparation of the optically active compounds of the formula (V) is carried out, the acid-binding agents used are preferably lower tertiary alkylamines, cycloalkylamines, aralkylamines or arylamines. Suitable examples are triethylamine, N,N-dimethylbenzylamine, pyridine, 1,4-diazabicyclo[2.2.2]octane and 1,5-diazabicyclo[4.3.0]non-5-ene.

When the third step of the process for the preparation of the optically active compounds of the formula (V) is carried out, the diluents used can be all organic solvents customary for this type of reaction. Preferably, halogenated hydrocarbons, such as methylene chloride, chloroform and carbon tetrachloride, can be used.

When the third step of the process for the preparation of the optically active compounds of the formula (V) is carried out, the reaction temperatures can be varied within a certain range. In general, the reaction is carried out at temperatures between 0° C. and 100° C., preferably between 0° C. and 50° C.

When the third step of the process for the preparation of the optically active compounds of the formula (V) is carried out, in general 1 to 1.3 moles of sulphonic acid derivative of the formula (XI) and also 1 to 1.3 moles of acid-binding agent are used per mole of optically active diol of the formula (X). The workup is carried out by conventional methods. In general, the procedure is such that the reaction mixture is first washed with weakly acidic and then with weakly basic aqueous solution, then dried and concentrated. The resulting product can be used without additional purification for the subsequent reaction.

Formula (XIII) provides a general definition of the triazole salts required as reaction components, when the fourth step of the process for the preparation of the optically active compounds of the formula (V) is carried out. Preference is given to those substances in which $Me^1$ represents sodium or potassium.

The triazole salts of the formula (XIII) are known.

When the fourth step of the process for the preparation of the optically active compounds of the formula (V) is carried out, the acid-binding agents used can be all conventional organic and inorganic bases.

Preferably, alkali metal carbonates, such as, for example, sodium carbonate or sodium bicarbonate, furthermore lower tertiary alkylamines, cycloalkylamines, arylalkylamines or arylamines, such as, for example, triethylamine, N,N-dimethylbenzylamine, pyridine, 1,4-diazabicyclo[2.2.2]octane or 1,5-diazabicyclo[4.3.0]non-5-ene, can be used.

When the fourth step of the process for the preparation of the optically active compounds of the formula (V) is carried out, the diluents used can be all inorganic solvents customary for this type of reaction. Preferably, polar, aprotic diluents, such as dimethylformamide and dimethyl sulphoxide, can be used.

When the fourth step of the process for the preparation of the optically active compounds of the formula (V) is carried out, the reaction temperatures can be varied in a fairly large range. In general, the reaction is carried out at temperatures between 20° C. and 150° C., preferably between 50° C. and 150° C.

The reactions in the fourth step of the process for the preparation of the optically active compounds of the formula (V) are, if desired, carried out under an inert gas atmosphere, such as, for example, under nitrogen or argon.

When the fourth step of the process for the preparation of the optically active compounds of the formula (V) is carried out, in general 2 to 4 moles of triazole salt of the formula (XIII) are used per mole of optically active compound of the formula (XII). The workup is carried out by conventional methods. In general, the procedure is such that water and also an organic solvent which has low solubility in water, if necessary after first distilling off the diluent, are added to the reaction mixture, the organic phase is separated off, dried and concentrated, and the remaining residue is purified by chromatography.

The procedure of the process according to the invention is illustrated by the examples which follow.

EXAMPLE 1

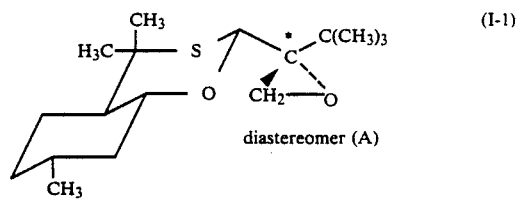

diastereomer (A)

14.56 g (130 mmol) of potassium tert.-butylate are added in portions at a temperature of 10° C. under a nitrogen atmosphere and with stirring to a solution of 25.0 g (88 mmol) of oxathiane ketone of the formula

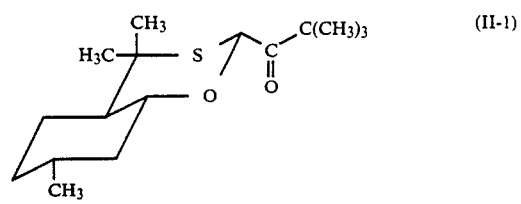

and 28.6 g (130 mmol) of trimethylsulphoxonium iodide in 150 ml of absolute tert.-butanol. The mixture is then stirred for another hour at 10° C. and subsequently for 16 hours at room temperature. The reaction mixture is worked up by concentrating it under reduced pressure, pouring the remaining residue into water and extracting the resulting mixture with dichloromethane. The combined organic phases are dried over sodium sulphate and concentrated under reduced pressure. In this manner, 25.6 g (98% of theory) of a product which, according to analysis by gas chromatography, consists of 93% of the diastereomer (A) of the formula (I-1) and of 7% of the diastereomer (B), are obtained (d.e. 86%)

The diastereomers can be separated by chromatography over silica gel using petroleum ether/diethyl ether=5:2 as eluent. This gives the pure diastereomer (A) of the formula (I-1) in a yield of 61% of theory.

Diastereomer (A)

$R_F$ value 0.46 (silica gel; petroleum ether/diethyl ether=5:1)

IR spectrum (NaCl): 3060 cm$^{-1}$ (=CH)

$^1$H-NMR spectrum (360 MHz, CDCl$_3$)

Characteristic signals: δ=0.9 (d, 3H, C$\underline{H}_3$—CH); 0.99 (s, 9H, t-butyl); 1.23 and 1.43 (both s, both 3H, C$\underline{H}_3$—C—C$\underline{H}_3$); 2.82 and 2.98 (dd, J=5.2 Hz, 2H, CH$_2$—$\overset{O}{\diagup \diagdown}$ ); 3.38 (d of t, 1H, —C$\underline{H}$—OR); 5.48 (s, 1H, —S—C$\underline{H}$—O—)

Mass spectrum: m/e=298 (2%, M$^+$)

Diastereomer (B)

$R_F$ value 0.29 (silica gel; petroleum ether:diethyl ether=5:1)

$^1$H-NMR spectrum (360 MHz, CDCl$_3$)

Characteristic signals: δ=0.91 (d, 3H, C$\underline{H}_3$—CH); 1.04 (s, 9H, t-butyl); 1.24 and 1.43 (both s, both 3H, C$\underline{H}_3$—C—C$\underline{H}_3$); 2.71 and 2.93 (dd, J=4.7 Hz, CH$_2$—$\overset{O}{\diagup \diagdown}$ ); 3.39 (d of t, 1H, —C$\underline{H}$—OR); 5.30 (s, 1H,

—S—CH—O—).

Mass spectrum: m/e=298 (2%, M$^+$)

EXAMPLE 2

(V-1) S-enantiomer

1st step (VIII-1) diastereomer (A)

6.4 g (0.27 mol) of sodium hydride (=8.0 g of 80% strength sodium hydride) are added to a solution of 43.1 g (0.34 mol) of 4-chlorophenol in 80 ml of absolute dimethylformamide, and the mixture is stirred at 25° C. for 30 minutes. A solution of 25 g (84 mmol) of optically active oxirane according to Example 1 (crude product) in 50 ml of dimethylformamide is then added dropwise. The mixture is stirred for another 30 minutes at 25° C. and another hour at 120° C. The reaction mixture is then filtered off with suction and the filtrate is concentrated under reduced pressure. The residue remaining is poured into a mixture of ice water and dichloromethane. The organic phase is separated off, the aqueous phase is extracted twice with dichloromethane, the combined organic phases are washed twice with 10% strength aqueous sodium hydroxide solution and then with aqueous sodium chloride solution. After drying over sodium sulphate, the organic phase is concentrated under reduced pressure. This gives 32.3 g of a product of which 90% consists of the two diastereomers of the above formula, 91.5% of diastereomer (A) and 8.5% of diastereomer (B) being present in the mixture of diastereomers (83% d.e.).

Spectroscopic data of the mixture of diastereomers:

IR spectrum (NaCl): 3600-3300 cm$^{-1}$ (OH); 1600, 1580 cm$^{-1}$ (C=C)

$^1$H-NMR spectrum (360 MHz, CDCl$_3$):

Characteristic signals: δ=2.83 and 2.97 (O$\underline{H}$); 3.30-3.50 (m, 1H, —C$\underline{H}$—OR); 4.07 and 4.21 (both dd, HO—$\overset{|}{\underset{|}{C}}$—CH$_2$—);

5.23 and 5.37 (both s, —S—C$\underline{H}$—O—); 6.80–6.97 and 7.22–7.30 (4H, aromatic H).

Mass spectrum (identical for both diastereomers): m/e 426 (M$^+$ missing); 369 (0.5%, M$^+$-t-butyl), 199 (100%, oxathiane fragment).

2nd step (X-1) S-enantiomer

A solution of 31.9 g (75 mmol) of the crude product of diastereomer (A) of the formula (VIII-1) in 250 ml of acetonitrile is added with stirring to a mixture of 23.9 g (0.18 mol) of N-chlorosuccinimide, 25.4 g (0.15 mol) of silver nitrate, 20.0 g (0.24 mol) of sodium bicarbonate, 800 ml of acetonitrile and 150 ml of water, which had been warmed to 40°–50° C. The mixture is stirred for another 15 minutes at 40° to 50° C., 78 ml of saturated, aqueous sodium sulphite solution and 78 ml of saturated, aqueous sodium chloride solution are added dropwise in succession, the mixture is filtered off with suction and the residue is washed with a mixture of methylene chloride/hexane=1:1.

The filtrate is extracted twice with the same volume each time of a mixture of methylene chloride/hexane=1:1. The organic phase is separated off, washed with saturated, aqueous sodium bicarbonate solution, dried over sodium sulphate, concentrated under reduced pressure and subsequently freed from any solvent residues present in a high vacuum. The product thus formed which predominantly consists of optically active α-hydroxyaldehyde of the formula

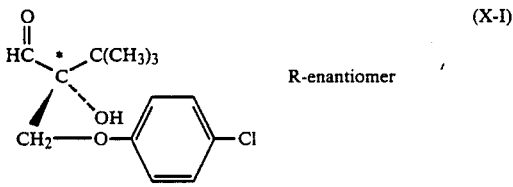

is dissolved in 250 ml of absolute diethyl ether and added dropwise at room temperature with stirring to a suspension of 14.1 g (0.37 mol) of lithium aluminum hydride in 250 ml of absolute diethyl ether. The reaction mixture is heated to reflux for 3 hours, 25 ml of ethyl acetate, 25 ml of 4N aqueous sodium hydroxide solution and 25 ml of water are then added dropwise in succession, the solid is filtered off with suction and washed with diethyl ether, the organic phase is dried over sodium sulphate and concentrated under reduced pressure.

In this manner, 12.9 g of a product consisting, according to analysis by gas chromatography, of 60% of the optically active diol of the formula (X-1) are obtained.

IR spectrum (NaCl):
OH band at 3100–3600 cm$^{-1}$.
C=C bands at 1600 and 1590 cm$^{-1}$.
Mass spectrum: m/e=259 (20%, M+)

3rd step

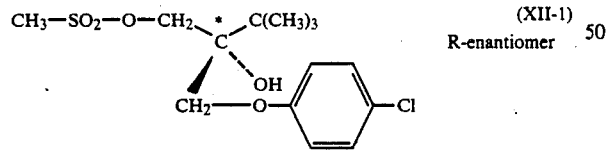

A solution of 5.0 g (44 mol) of methanesulphonyl chloride in 10 ml of absolute methylene chloride and a solution of 4.4 g (44 mmol) of triethylamine in 10 ml of absolute methylene chloride are simultaneously added dropwise under a nitrogen atmosphere at 0° C. with stirring to a solution of 12.7 g of the crude product of R-enantiomer of the formula (X-1) in 20 ml of absolute methylene chloride. Stirring is continued at 0° C. for 4 hours, and the mixture is then warmed to 25° C. The reaction mixture is successively extracted with saturated, aqueous citric acid solution and with saturated, aqueous sodium bicarbonate solution, and the organic phase is dried over sodium sulphate and concentrated under reduced pressure. In this manner, 16.9 g of the R-enantiomer of the formula (XII-1), which is further reacted without additional purification, are obtained.

IR spectrum (NaCl): OH band 3600–3200 cm$^{-1}$; CH$_3$—SO$_2$—O—CH$_2$ bands 1360 and 1180 cm$^{-1}$ 4th step

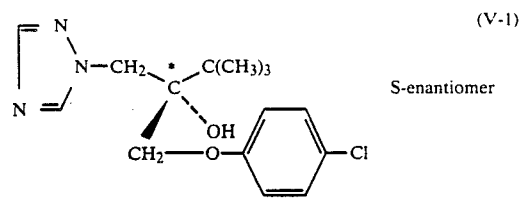

A mixture of 16.4 g of the crude product of the R-enantiomer of the compound of the formula (XII-1), 13.3 g of the sodium salt of triazole and 50 ml of absolute dimethylformamide is stirred at 120° C. under a nitrogen atmosphere for 4 hours. The mixture is then concentrated under reduced pressure, and the residue remaining is added to a mixture of water and methylene chloride. The organic phase is separated off, the aqueous phase is extracted twice with methylene chloride, the combined organic phases are dried over sodium sulphate and concentrated. 9.04 g of a product remain which is purified by column chromatography over 350 g of silica gel using a mixture of methylene chloride/methanol=95:5 as the eluent. Concentration of the eluate gives 4.43 g (29% of theory) of a product containing, according to analysis by liquid chromatography, 93.5% of the S-enantiomer of 2-(4-chlorophenoxymethyl)-3,3-dimethyl-1-(1,2,4-triazol-1-ylmethyl)-2-butanol. (Optical purity 87% e.e.)

It is understood that the specification and examples are illustrative but not limitative of the present invention and that other embodiments within the spirit and scope of the invention will suggest themselves to those skilled in the art.

I claim:

1. An optically active oxirane of the formula

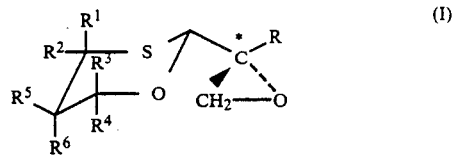

in which
R represents a straight-chain or branched alkyl having 1 to 6 carbon atoms, which is unsubstituted or substituted by at least one of halogen, alkoxy having 1 to 4 carbon atoms, alkylthio having 1 to 4 carbon atoms, the CHO group or a derivative thereof, phenoxy and phenyl, represents cycloalkyl having 3 to 8 carbon atoms, which is unsubstituted or substituted by at least one of alkyl having 1 to 4 carbon atoms, alkoxy 1 to 4 carbon atoms and halogen or represents phenyl, which is unsubstituted or substituted by at least one of alkyl having 1 to 4 carbon atoms, alkoxy having 1 to 4 carbon atoms, alkylthio having 1 to 4 carbon atoms and halogen,
$R^1$, $R^2$, $R^3$, $R^4$, $R^5$ and $R^6$ represent hydrogen or alkyl having 1 to 4 carbon atoms, at least one of these radicals representing alkyl having 1 to 4 carbon atoms, or R⁴ and R⁵ together may represent alkanediyl having 3 to 6 carbon atoms, which is unsubstituted or monosubstituted to trisubstituted by identical or different alkyl substituents having 1 to 4 carbon atoms, or R⁴ and R⁵ together with the adjacent carbon atoms may represent a fused bicyclic hydrocarbon having 7 or 8 carbon atoms which is unsubstituted or monosubstituted to trisubstituted by identical or different alkyl substituents having 1 to 4 carbon atoms.

2. An optically active oxirane according to claim 1, of the formula

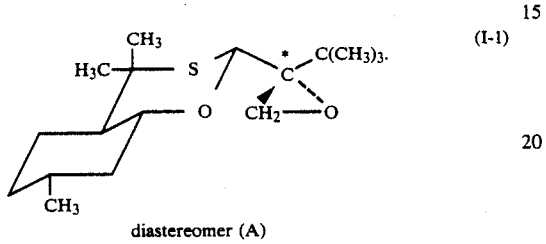

diastereomer (A)

3. An optically active oxirane according to claim 1, in which

R represents alkyl having 1 to 4 carbon atoms, which is unsubstituted or substituted by at least one of fluorine, chlorine, bromine, alkoxy having 1 or 2 carbon atoms, dioxolanyl, formyl, methoximinomethyl, alkylthio having 1 or 2 carbon atoms, phenoxy and phenyl, represents cycloalkyl having 3 to 7 carbon atoms, which is unsubstituted or substituted by at least one of alkyl having 1 to 2 carbon atoms, alkoxy having 1 or 2 carbon atoms, alkylthio having 1 or 2 carbon atoms, fluorine, chlorine and bromine or represents phenyl, which is unsubstituted or substituted by at least one of alkyl having 1 or 2 carbon atoms, alkoxy having 1 or 2 carbon atoms, alkylthio having 1 or 2 carbon atoms, fluorine, chlorine and bromine and R¹, R², R³, R⁴, R⁵ and R⁶ represent hydrogen, methyl or ethyl, where, however, at least one of these radicals represents methyl or ethyl, or furthermore R⁴ and R⁵ together may represent alkanediyl having 3 to 5 carbon atoms, which is unsubstituted or monosubstituted to trisubstituted by identical or different substituents from the group consisting of methyl and ethyl, or furthermore R⁴ and R⁵ together with the adjacent carbon atoms may represent a fused bicyclic hydrocarbon having 7 or 8 carbon atoms, which is unsubstituted or monosubstituted to trisubstituted by identical or different substituents from the group consisting of methyl and ethyl.

4. An optically active oxirane according to claim 1, in which

R represents methyl, ethyl, isopropyl or tert.-butyl, which is unsubstituted or monosubstituted or disubstituted by identical or different substituents from the group consisting of fluorine, chlorine, bromine, methoxy, methylthio, methoximinomethyl, phenoxy and phenyl, furthermore represents the grouping

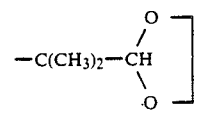

furthermore represents cyclopropyl, cyclopentyl or cyclohexyl, each of which is unsubstituted or monosubstituted or disubstituted by identical or different substituents from the group consisting of methyl, methylthio, fluorine and chlorine, or represents phenyl which is unsubstituted or monosubstituted or disubstituted by identical or different substituents from the group consisting of methyl, methoxy, methylthio, fluorine and chlorine, and the oxathiane moiety represents a grouping of the formula

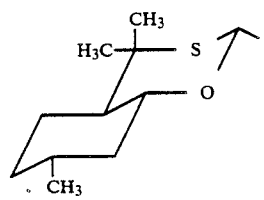

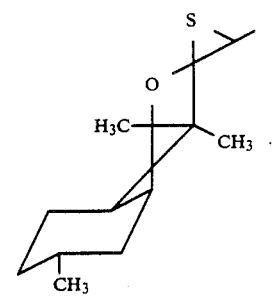

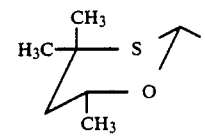

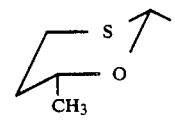

or

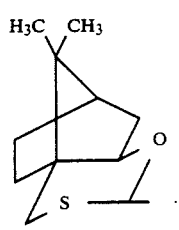

* * * * *